US008688215B2

(12) United States Patent
Whinnett et al.

(10) Patent No.: US 8,688,215 B2
(45) Date of Patent: Apr. 1, 2014

(54) APPARATUS AND METHOD FOR PROGRAMMING A PACEMAKER

(75) Inventors: Zachary Ian Whinnett, London (GB); Darrel P. Francis, Harrow (GB); Justin E. R. Davies, London (GB); Keith Wilson, East Sussex (GB); Jamil Mayet, London (GB)

(73) Assignee: Imperial Innovations Limited (GB)

( * ) Notice: Subject to any disclaimer, the term of this patent is extended or adjusted under 35 U.S.C. 154(b) by 1219 days.

(21) Appl. No.: 11/572,339

(22) PCT Filed: Jul. 21, 2005

(86) PCT No.: PCT/GB2005/002869
§ 371 (c)(1),
(2), (4) Date: Sep. 15, 2008

(87) PCT Pub. No.: WO2006/008535
PCT Pub. Date: Jan. 26, 2006

(65) Prior Publication Data
US 2009/0069859 A1    Mar. 12, 2009

(30) Foreign Application Priority Data

Jul. 21, 2004    (GB) .................................. 0416320.0

(51) Int. Cl.
*A61N 1/00*      (2006.01)
(52) U.S. Cl.
USPC ........................................................... 607/23
(58) Field of Classification Search
USPC ........................................................... 607/23
See application file for complete search history.

(56) References Cited

U.S. PATENT DOCUMENTS

| 5,540,727 | A | 7/1996 | Tockman et al. |
| 5,862,803 | A | 1/1999 | Besson et al. |
| 6,491,639 | B1 | 12/2002 | Turcott |
| 6,832,113 | B2 * | 12/2004 | Belalcazar ..................... 607/23 |
| 2003/0074029 | A1 | 4/2003 | Deno et al. |
| 2003/0097158 | A1 | 5/2003 | Belalcazar |

FOREIGN PATENT DOCUMENTS

| JP | 2002-177248 A | 6/2002 |
| WO | 03077991 A1 | 9/2003 |

OTHER PUBLICATIONS

Nora Linder, "International Application No. PCT/GB2005/002869 'International Preliminary Report on Patentability and Written Opinion'", Jan. 23, 2007, Publisher: PCT.

* cited by examiner

*Primary Examiner* — Christopher D Koharski
*Assistant Examiner* — Nadia Ahmad
(74) *Attorney, Agent, or Firm* — Kaplan Breyer Schwarz & Ottesen, LLP

(57) ABSTRACT

A pacemaker optimising apparatus comprising: a component (4) which noninvasively or invasively monitors a haemodynamic measurement continuously in an individual and a processor (15) for receiving the haemodynamic measure and generating a pacemaker programming signal in response to this. There is also provided a communication device (17) for sending the pacemaker programming signal to the control system of the pacemaker (2). There is also a method for an efficient process by which this apparatus can automatically use the haemodynamic measurements to determine the ideal settings for a particular pacemaker in a particular individual, and to updates the pacemaker's settings accordingly.

9 Claims, 8 Drawing Sheets

APPARATUS AND METHOD FOR PROGRAMMING A PACEMAKER

The present invention relates to a pacemaker programming apparatus, a computer program therefor and a method of programming a pacemaker.

In the field of cardiology, one condition that is known to afflict patients is the existence of a slow heartbeat. This can lead to dizziness, dyspnoea, fainting or even the death of the patient. There can be many different causes for a slow heartbeat. Some causes, such as the blocking of arteries leading to the heart's conduction system can, themselves, be treated in order to return a regular heart rate to the patient. Otherwise, the treatment for a slow heartbeat is typically to fit the patient with a pacemaker, and, more specifically, a standard dual chamber pacemaker.

One side effect of ventricular pacing is a collection of symptoms, such as decreased cardiac output, that are known as "pacemaker syndrome". It has been reported (Szabados, S. et al. Orv Hetil 1994, 135, 23, 1255-8) that a non-invasive continuous blood pressure recorder, the Finapres 2300, can be used in the diagnosis of pacemaker syndrome.

It is also known to fit pacemakers to patients suffering from conditions other than a slow heart rate. In particular, in patients suffering from chronic heart failure where the walls of the ventricles (the main pumping chambers of the human heart) are no longer synchronised, another class of pacemaker, known as a biventricular (or resynchronising) pacemaker, can be used to effect cardiac resynchronisation therapy. A biventricular pacemaker stimulates both the left and right sides of the heart in order to shorten atrioventricular delay[1,2] and improve synchrony of ventricular contractions[3,4] but does not necessarily vary the heart rate per se. The fitting of a biventricular pacemaker to an appropriate patient has been observed to result in a prompt improvement in haemodynamic status[5,6,7,8], with an increase in peak rise in intraventricular pressure[10,2], an increase in stroke volume[11] and consequently higher systemic arterial blood pressure[12].

In principle, there are, in fact, two classes of biventricular pacemaker. An atriobiventricular pacemaker has the following three basic attributes, whose settings may be adjusted.

1) The heart rate. In many patients with resynchronizing pacemakers, the patient's natural heart rate is satisfactory, and the pacemaker is programmed merely to follow the natural heart rate. In other patients, the natural heart rate is too low, and the pacemaker is programmed to pace at a higher rate. In both groups of patients, the pacemaker may change between following the natural heart rate and actively controlling the heart rate, for example when the patient undertakes physical exertion.

2) The atrioventricular ("AV") delay. This is the time interval between the atrium and the ventricles getting electrical stimulation. This delay is often set at about 120 ms when the pacemaker is initially implanted.

3) The left ventricle versus right ventricle ("LV-RV" or simply "VV") delay. This is the time interval between the left ventricle and the right ventricle getting electrical stimulation. It is often set at 0 ms when the pacemaker is manufactured. Some manufacturers have a small non-zero lower limit, such as 4 ms, which can be treated as 0 ms for practical purposes.

The other class of biventricular pacemaker has two ventricular leads but, unlike the atrioventricular pacemaker, only the setting of VV delay can be adjusted and not the setting of AV delay.

In contrast, in a standard dual chamber pacemaker with an atrial lead and a (single) ventricular lead only the setting of the AV delay can be adjusted but not the setting of the VV delay.

In order to provide the optimum settings for these attributes, and especially atrioventricular (AV) delay, in a particular patient, many centres use an echocardiographic approach to selecting pacemaker programming. The most commonly used method is to determine, at resting heart rate, the longest filling time associated with complete atrial systole uninterrupted by ventricular systole[19,20,21]. However, one problem with this approach is that there is little data to suggest that this approach optimizes hemodynamics in patients with chronic heart failure who have resynchronizing pacemakers[22].

It has been observed that blood pressure rises with the onset of biventricular pacing, and therefore it is theoretically possible to optimize the activity of a biventricular pacemaker by adjusting the attributes of the pacemaker while measuring the blood pressure of the patient. The problem with using a regular sphygmomanometer with an arm band cuff in order to measure blood pressure in these situations would be that taking each blood pressure measurement requires a considerable amount of time and, in practice, many different measurements would have to be taken during the optimisation process. Thus optimization by this method is entirely impractical.

It has also been proposed to determine blood pressure while optimizing biventricular pacemaker attributes by invasive haemodynamic monitoring of the blood pressure of the patient[6]. However, the problem with this approach is that the clinical intricacy involved and the non-trivial risk associated with invasive blood pressure monitoring make it unsuitable for routine optimization of pacemaker attribute settings in normal practice.

Furthermore, a previously unrecognised problem in each of the above approaches to pacemaker optimization is that they assume that optimizing an attribute of the pacemaker is effective when the patient has a resting heart rate.

In addition, the previous approaches also suffer from the problem that there is physiological noise when measurements (either echocardiography or blood pressure measurements) are taken. For example, the prior art approaches do not take account of the random drift in blood pressure which naturally occurs over time.

The present invention seeks to alleviate one or more of the above problems and is applicable to one or more classes of pacemaker (i.e. standard dual chamber pacemakers and either class of biventricular pacemaker).

According to one aspect of the present invention, there is provided a pacemaker programming apparatus comprising:
  a monitoring device capable of determining a haemodynamic measure of an individual at each heart beat of the individual and generating a haemodynamic measure indication signal related to the haemodynamic measure; and
  a processor for receiving the haemodynamic measure indication signal and generating a pacemaker programming signal in response to the haemodynamic measure indication signal.
  Preferably the apparatus also comprises a communication device for sending the pacemaker programming signal to a pacemaker.
  A preferred monitoring device comprises:
  a contractible cuff for receiving a body extremity of an individual;

a light source directable upon a body extremity received in the contractible cuff; and a light sensor for detecting light from the light source, the light sensor being located such that a body extremity received in the contractible cuff interposes between the light source and the light sensor, the light sensor being capable of generating the haemodynamic measure indication signal in response to the intensity of light detected from the light source.

Alternatively, the monitoring device comprises another form of non-invasive monitoring device, such as a pulse oximeter or a bio-impedance monitor which detects changes in impedance during the cardiac cycle, which are indicative of stroke volume. Alternatively, the monitoring device is invasive. In some embodiments, the blood pressure monitoring device is a component in the implanted pacemaker system (such as an accelerometer or a Doppler Beam). In other embodiments, it is a separate invasive monitoring device.

Conveniently, the processor generates the pacemaker programming signal by determining the change in a haemodynamic measure, derived from the haemodynamic measure indication signal of the individual, due to adjustment of a setting of an attribute of the pacemaker.

According to another aspect of the present invention, there is provided a pacemaker programming apparatus comprising:

a processor capable of generating a pacemaker programming signal in response to a haemodynamic measure indication signal; and a communication device for sending the pacemaker programming signal to a pacemaker in an individual, wherein the processor generates the pacemaker programming signal by determining the change in a haemodynamic measure derived from the haemodynamic measure indication signal of the individual due to adjustment of a setting of an attribute of the pacemaker.

Preferably, the haemodynamic measure indication signal is indicative of the haemodynamic measure at a first raised heart rate.

According to a further aspect of the present invention, there is provided a pacemaker programming apparatus comprising:

a processor capable of generating a pacemaker programming signal response to a haemodynamic measure indication signal; and a communication device for sending the pacemaker programming signal to a pacemaker in an individual, wherein the haemodynamic measure indication signal is indicative of a haemodynamic measure of the individual at a first raised heart rate.

Advantageously the processor is capable of generating a pacemaker programming signal in response to the haemodynamic measure of the individual at the first raised heart rate and haemodynamic measure of the individual at a second raised heart rate.

Preferably, the apparatus further comprises an artefact sensor, in communication with the processor, for detecting the phase of respiration and/or body movements of the individual. It is particularly preferred that the artefact sensor comprises a strain gauge.

According to another aspect of the present invention, there is provided a computer program for a pacemaker programming apparatus comprising:

a testing module containing code for receiving a haemodynamic measure indication signal obtained during adjustment of the setting of a first attribute of a pacemaker in an individual;

a determination module containing code for determining from the haemodynamic measure indication signal the change in haemodynamic measure of the individual during adjustment of the setting of the first attribute of the pacemaker; and a setting selection module containing code for selecting a setting of the first attribute in response to the change in the haemodynamic measure of the individual.

Conveniently the testing module comprises:

a first module containing code for selecting a setting of the first attribute of the pacemaker;

a second module containing code for receiving a blood pressure indication signal obtained from the individual;

a third module containing code for recording the setting of the first attribute and the respective blood pressure indication signal; and a fourth module containing code for instructing the first, second and third modules to repeat their activity, a predetermined number of times, at least one different setting of the first attribute, and wherein the determination module contains code for determining the change in a haemodynamic measure of the individual caused by each setting of the first attribute; and the setting selection module contains code for selecting the setting of the first attribute in response to its respective change in the haemodynamic measure blood pressure of the individual.

Preferably, the computer module further comprises an attribute selection module containing code for selecting the first attribute and instructing the testing module to operate on the selected first attribute.

Advantageously, the attribute selection module contains code for selecting the first attribute and instructing the testing module, the determination module and the setting selection module to operate on the first attribute and then selecting a second attribute and instructing the testing module, the determination module and the setting selection module to operate on the second attribute.

Conveniently, the first module also contains code for selecting a setting of a second attribute of the pacemaker in the individual;

the third module contains code for recording the combination of the settings of the first and second attributes and the respective blood pressure indication signal;

the fourth module contains code for instructing the first, second and third modules to repeat their activity, a number of times, at least one different setting of the first and/or second attribute;

the determination module contains code for determining the change in a haemodynamic measure of the individual caused by each combination of the settings of the first and second attributes; and the setting selection module contains code for selecting the settings of the first and second attributes in response to their respective changes in the haemodynamic measure of the individual.

Preferably, the first attribute is one of the AV delay and the VV delay and the second attribute is the other of the AV delay and the VV delay.

Advantageously, the first attribute is one of the AV delay and the VV delay.

Conveniently, the fourth module contains code for instructing the first module to select the same setting of the first attribute, and optionally the second attribute, at alternate repeats of its activity.

Preferably, the fourth module contains code for instructing the first module to select a different setting of the first attribute, and optionally the second attribute, at each repeat of its activity.

Advantageously, the computer program further comprises a heart beat detection module containing code for receiving a signal indicative of the heart rate of the individual and instructing the first, second and third modules to carry out each repeat of their activity for a length of time equivalent to a number of heart beats of the individual.

Conveniently, the number of heart beats is 10.

According to another aspect of the present invention there is provided a computer program for a pacemaker programming apparatus comprising:

a testing module containing code for receiving a haemodynamic measure indication signal obtained during adjustment of the setting of a first attribute of a pacemaker in an individual at raised heart rate;

a setting selection module containing code for selecting a setting of the first attribute in response to the haemodynamic measure indication signal.

Conveniently, the testing module comprises:

a first module containing code for selecting a setting of the first attribute of the pacemaker;

a second module containing code for receiving a haemodynamic measure indication signal obtained from the individual;

a third module containing code for recording the setting of the first attribute and the respective haemodynamic measure indication signal; and a fourth module containing code for instructing the first, second and third modules to repeat their activity, a number of times, at least one different setting of the first attribute, and wherein the setting selection module contains code for selecting the setting of the first attribute in response to its respective haemodynamic measure indication signal.

Preferably, the computer program further comprises an attribute selection module containing code for selecting the first attribute and instructing the testing module to operate on the selected first attribute.

Advantageously, the attribute selection module contains code for selecting the first attribute and instructing the testing module and the setting selection module to operate on the first attribute and then selecting a second attribute and instructing the testing module and the setting selection module to operate on the second attribute.

Conveniently, the first module also contains code for selecting a setting of a second attribute of the pacemaker in the individual;

the third module contains code for recording the combination of the settings of the first and second attributes and the respective haemodynamic measure indication signal;

the fourth module contains code for instructing the first, second and third modules to repeat their activity, a predetermined number of times, at least one different setting of the first and/or second attribute; and the setting selection module contains code for selecting the settings of the first and second attributes in response to their respective haemodynamic measure indication signals.

Preferably, the first attribute is one of the AV delay and the VV delay and the second attribute is the other of the AV delay and the VV delay.

Advantageously, the first attribute is one of the AV delay and the VV delay.

Conveniently, the fourth module contains code for instructing the first module to select the same setting of the first attribute, and optionally the second attribute, at alternate repeats of its activity.

Preferably, the fourth module contains code for instructing the first module to select a different setting of the first attribute, and optionally the second attribute, at each repeat of its activity.

Advantageously, the computer program further comprises a heart beat detection module containing code for receiving a signal indicative of the heart rate of the individual and instructing the first, second and third modules to carry out each repeat of their activity for a length of time equivalent to a number of heart beats of the individual.

Advantageously, the number of heart beats is 10.

Conveniently, the computer program further comprises a determination module containing code for determining, from the blood pressure indication signal, the change in a haemodynamic measure of the individual during adjustment of the setting of the first attribute, and optionally the second attribute, of the pacemaker and wherein the setting selection module contains code for selecting a setting of the first attribute, and optionally the second attribute, in response to the change in the haemodynamic measure of the individual.

Preferably, the setting selection module contains code for selecting the setting of the first attribute or the settings of the first and second attributes by interpolating between the respective changes in the haemodynamic measure of the individual or the blood pressure indication signals at the settings selected by the first module of the testing modules.

Advantageously, the setting selection module contains code to interpolate by fitting the changes in the haemodynamic measure of the individual or the blood pressure indication signals at the settings selected by the first module of the testing module to a parabola.

Conveniently, the computer program further comprises a programming module containing code for generating a pacemaker programming signal for setting a pacemaker to the setting of the first attribute, and optionally the second attribute, selected by the setting selection module.

Preferably the fourth module contains code for instructing the first, second, and third modules to alternate their activity between two settings of the first and/or second attribute.

Advantageously, the fourth module contains code for instructing the first, second and third modules to alternate their activity between the two settings a predetermined number of times, preferably three times.

Conveniently, the fourth module contains code for selecting the number of times for alternating the activity of the first, second and third modules between the two settings, in response to comparing the haemodynamic measure of the individual at successive measurements of the or each attribute at the same setting. It is preferred that this occurs by increasing number of times for alternating the activity, in response to successive measurements of the or each attribute at the same setting being substantially different and by decreasing the number of times for alternating the activity, in response to successive measurements of the or each attribute at the same setting being substantially similar. By "substantially different" is meant more than 1%, 2%, 5%, 10%, 20%, 30%, 40% or 50% different from each other. By "substantially similar" is meant less than 1%, 2%, 5%, 10%, 20%, 30%, 40% or 50% different from each other.

Preferably, the computer program further comprises a respiratory cycle detection module containing code for receiving a signal indicative of the respiratory cycle of the individual and instructing the first, second and third modules to carry out each repeat of their activity for a length of time related to the detected length of the respiratory cycle.

Advantageously, the respiration cycle detection module contains code for instructing the first, second and third modules to carry out each repeat of their activity for the length of time of one complete respiratory cycle of the individual.

Conveniently, the computer program further comprises a heart beat detection module containing code for receiving a signal indicative of the heart rate of the individual and for instructing one or more of the modules such that at least the determination module omits determining the change in the haemodynamic measure for at least the first heart beat of the individual at each setting of the first and/or second attribute, and preferably the first two heart beats.

According to another aspect of the present invention there is provided a pacemaker programming apparatus as described above wherein the processor is programmed with a computer program as previously described.

According to a further aspect of the present invention there is provided a method of programming a pacemaker in an individual comprising the steps of:
  determining a haemodynamic measure of the individual while adjusting the setting of a first attribute of the pacemaker;
  selecting a setting of the first attribute of the pacemaker in response to the haemodynamic measure; and
  adjusting the attribute of the pacemaker to the selected setting.

According to another aspect of the present invention there is provided a method of programming a pacemaker in an individual comprising the steps of:
  determining the change in a haemodynamic measure of the individual while adjusting the setting of a first attribute of the pacemaker;
  selecting a setting of the first attribute of the pacemaker in response to the change in the haemodynamic measure resulting from the setting;
  adjusting the attribute of the pacemaker to the selected setting.

Conveniently, the step of determining the change in the haemodynamic measure of the individual comprises the steps of
  constricting a body extremity of the individual;
  directing light on the constricted body extremity;
  detecting the light passing through the constricted body extremity.

According to yet another aspect of the present invention there is provided a method of programming a pacemaker in an individual comprising the steps of:
  raising the heart rate of the individual;
  determining a haemodynamic measure of the individual while the heart rate is raised and while adjusting a setting of a first attribute of the pacemaker;
  selecting a setting of the first attribute of the pacemaker in response to the haemodynamic measure; and
  adjusting the attribute of the pacemaker to the selected setting.

Preferably, the step of determining the haemodynamic measure of the individual comprises the steps of
  constricting a body extremity of the individual;
  directing light on the constricted body extremity;
  detecting the light passing through the constricted body extremity.

The haemodynamic measure, or the change thereof, may be determined invasively or non-invasively. Examples of the former are accelerometers or Doppler beams implanted with the pacemaker. Examples of the latter are a pulse oximeter or a bio-impedance monitor.

Advantageously, the step of determining the haemodynamic measure of the individual comprises determining the change in the haemodynamic measure of the individual.

Conveniently, the first attribute is one of the AV delay and the VV delay.

Preferably, the method further comprises the step of subsequently repeating the method with respect to a second attribute of the pacemaker of the individual.

Conveniently, the step of determining the haemodynamic measure or the change in the haemodynamic measure of the individual is carried out while adjusting the setting of the first attribute and adjusting the setting of a second attribute.

Preferably, the first attribute is one of the AV delay and the VV delay and the second attribute is the other of the AV delay and the VV delay.

Advantageously, the step of determining the haemodynamic measure or the change in the haemodynamic measure of the individual comprises the steps of: adjusting the first attribute, and optionally the second attribute, of the pacemaker between more than two settings.

Advantageously, the step of determining the haemodynamic measure or the change in the haemodynamic measure of the individual comprises alternating the setting of the first attribute, and optionally the second attribute, between a standard setting and one of a range of test settings.

Conveniently, the step of determining the haemodynamic measure or the change in the haemodynamic measure of the individual comprises adjusting the setting of the first attribute, and optionally the second attribute, between a range of test settings.

Preferably, the step of selecting a setting of a first attribute and optionally selecting the setting of a second attribute comprises interpolating between the haemodynamic measure or the change in haemodynamic measure that have been determined.

Advantageously, the interpolating step is carried out by fitting the haemodynamic measure or change in the haemodynamic measure that have been determined to the parabola.

Conveniently, the step of determining the haemodynamic measure or a change in haemodynamic measure while adjusting the setting of a first attribute, and optionally a second attribute, of the pacemaker comprises keeping the first attribute, and optionally the second attribute, at a particular setting for a number of heart beats while the haemodynamic measure or change in haemodynamic measure is determined.

Preferably, the number of heart beats is 10.

Conveniently, the settings of the first attribute, and optionally the second attribute, are alternated between two settings as the haemodynamic measure is determined.

Preferably, the settings are alternated are predetermined number of times, preferably three times.

Advantageously, the settings are alternated a number of times calculated in response to comparing the haemodynamic measure of the individual at successive measurements at the same setting.

Preferably, the settings are alternated an increased number of times in response to successive measurements at the same setting being substantially different and a decreased number of times in response to successive measurements at the same setting being substantially similar. By "substantially different" is meant more than 1%, 2%, 5%, 10%, 20%, 30%, 40% or 50% different from each other. By "substantially similar" is meant less than 1%, 2%, 5%, 10%, 20%, 30%, 40% or 50% different from each other.

Conveniently, the step of monitoring the respiratory cycle of the individual and wherein the determining of the haemodynamic measure or the change thereof of the individual is carried out for a length of time related to the detected length of the respiratory cycle.

Preferably, the step of determining the haemodynamic measure, or the change thereof, of the individual is carried out for the length of time of complete respiratory cycle of the individual.

Advantageously, the step of monitoring the heart beat of the individual and wherein the step of determining the haemodynamic measure, or the change thereof, of the individual is carried out omitting results from at least the first heart beat of the individual and preferably the first two heart beats of the individual at a setting of the first and/or second attribute of the pacemaker.

Conveniently, the steps of monitoring the phase of respiration and/or body movements of the individual and accounting for the effects of the phase of respiration and/or any body movements of the individual in the determination of the haemodynamic measure or the change thereof.

Advantageously, the haemodynamic measure is: the blood pressure of the individual; the absolute value of the blood pressure of the individual at one point in time or at a plurality of points in time; the change in blood pressure of the individual over a period of time; the stroke volume of the individual or the cardiac output of the individual.

Conveniently, the blood pressure of the individual is a systolic pressure, diastolic pressure, mean pressure, pulse pressure, rate of change of pressure, or peak rate of change of pressure.

Preferably, the pacemaker is a biventricular pacemaker, preferably an atriobiventricular pacemaker.

Thus embodiments of the present invention allow multiple measurements to be made at different heart rates and are more sensitive than echocardiography. Embodiments of the invention are simple and practical requiring little specialist skill and are thus less operator-dependent. Embodiments of the invention allow rapid assessment of hemodynamic effectiveness of cardiac resynchronization, without risk of complications. Embodiments of the invention permit testing (and retesting) in a variety of environments beyond the restricted environments that are mandatory for invasive testing. Furthermore, embodiments of the invention bring about more accurate optimization by testing at elevated heart rates and by determining a haemodynamic measure such as a change in blood pressure rather than necessarily the absolute blood pressure of a patient.

In this specification certain terms and phrases are used whose meaning will now be explained in greater detail.

The term "body extremity" means any digit, limb or other protuberance of the human body which has a pulse. It includes, but is not limited to, the fingers, thumbs and toes of a person.

The phrase "a haemodynamic measure indication signal" means a signal, such as a signal encoded in electronic form, which contains information concerning a characteristic of a haemodynamic measure of an individual. One example of a "haemodynamic measure indication signal" is a "blood pressure indication signal". For example, the characteristic might be the absolute blood pressure of an individual at a particular point in time; the absolute blood pressure of an individual at more than one point in time or the change in blood pressure of an individual over a period of time. Moreover the aspect of blood pressure addressed may be the systolic pressure, diastolic pressure, mean pressure, pulse pressure, rate of change of pressure, peak rate of change of pressure, or any other aspect of blood pressure which shows a significant improvement when biventricular pacing is applied. Finally, the term "blood pressure" includes a calculation, from the blood pressure signal, of an estimated stroke volume or cardiac output. One such method for this calculation is the MODELFLO method. Another is the Pressure Recording Analysis Method (PRAM method)[33].

The phrase "haemodynamic measure" means an indication derived from the haemodynamic measure indication signal of a patient. Accordingly, one example of a "haemodynamic measure" is "blood pressure". Thus, the haemodynamic measure might be an absolute value of the blood pressure of an individual at a particular point in time; the absolute value of the blood pressure of an individual at more than one point in time; the change in blood pressure of an individual over a period of time or another computation over time. The aspect of the blood pressure indication signal addressed may be the systolic pressure, diastolic pressure, mean pressure, pulse pressure, rate of change of pressure, peak rate of change of pressure, or any other aspect of blood pressure which can show a significant improvement when biventricular pacing is applied. Moreover, the haemodynamic measure may be something other than a blood pressure value per se. For example, it may be a calculation, from the blood pressure signal, of an estimated stroke volume or cardiac output. One such method for this calculation is the MODELFLO method which accompanies the Finapres device. Another is the Pressure Recording Analysis Method (PRAM method)[33].

It is therefore to be appreciated that the term "haemodynamic measure" wherever it appears in this specification may be replaced with the term "blood pressure" in order to refer to those specific embodiments.

The "change" in a haemodynamic measure means the relative difference in the measure in contrast to the absolute value of the measure.

The term "attribute of a pacemaker" means a particular characteristic of the function of the pacemaker and typically refers to one of the following: heart rate, AV delay or VV delay.

The phrase "setting of an attribute" means the level at which an attribute of a pacemaker is performing at a particular time. For example, the setting of the AV delay of a pacemaker might be 120 ms.

The phrase "a pacemaker programming signal" means a signal, such as a signal encoded electronically, which contains information sufficient for setting attributes of a pacemaker. For example, the information may be the setting for the heart rate; the atrioventricular (AV) delay; or the left ventricular versus right ventricular (VV) delay.

The phrase "adjustment of a pacemaker" means the changing of the setting of at least one attribute of the pacemaker.

The phrase "raised heart rate" means a heart rate greater than the heart rate of the individual when at rest (i.e. sitting or lying motionless). This could be achieved by pacing the heart, for example at 10% faster than the mean resting heart rate, or at a fixed heart rate faster than resting rate.

The term "state" when used in relation to a pacemaker means a particular combination of settings of the attributes of a pacemaker. For example, one state could be an AV delay of 120 ms and a VV delay of 0 ms.

The term "comprising" means "including" or "consisting of". Similarly, the term "comprises" means "includes" or "consists of".

In order that the present invention may be more readily understood, and so that further features thereof may be appreciated, embodiments of the invention will now be described, by way of example, with reference to the accompanying drawings which will now be explained.

Figure 3:
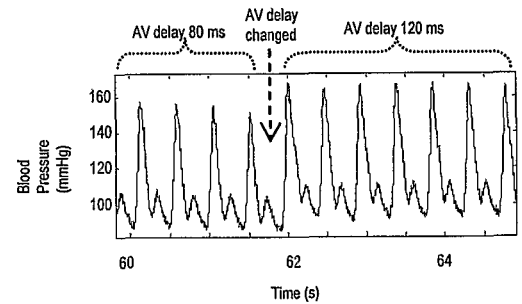
FIG. 3 is a graph showing a recording of the blood pressure response of a patient to changes in AV delay. The graph shows a prompt change in blood pressure when the AV delay is changed.
Figure 4:
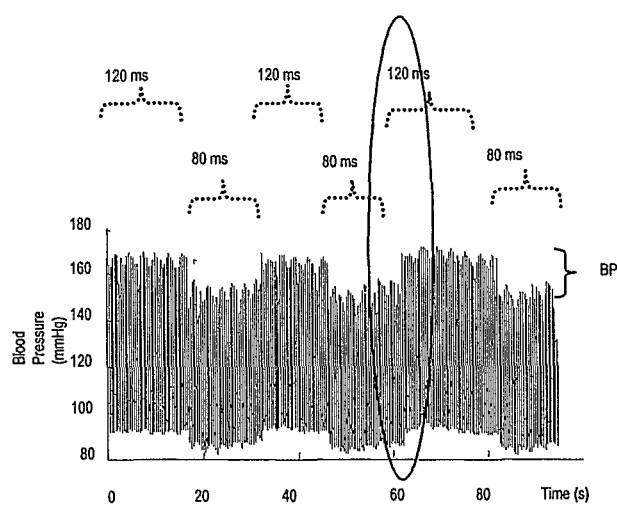

FIG. 4 is a graph showing a longer segment of the recording of FIG. 3. Several alternations of AV delay (between 80 ms and the reference value of 120 ms) give several replicate measures of ΔBP. The ellipse in FIG. 4 corresponds to the segment shown in FIG. 3.

Figure 5:
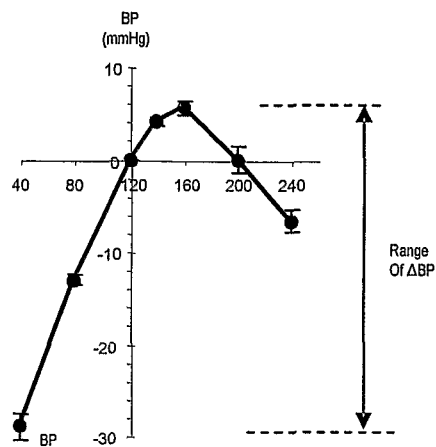

FIG. 5 is a graph showing how ΔBP varies in patient 3 of Table 1 as AV delay is varied from 40 to 240 ms.

Figure 6:
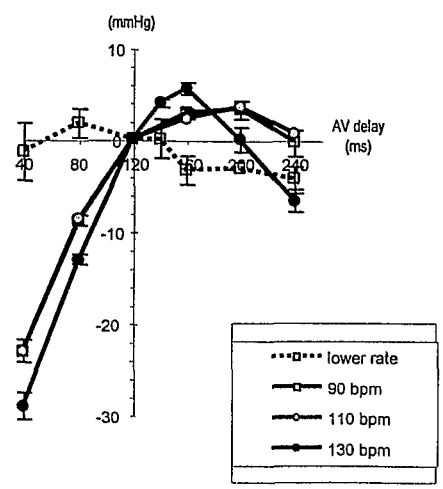

FIG. 6 is a graph as shown in FIG. 3 except that results are displayed for patient 3 of Table 1 at 4 different heart rates: rest, 90 bpm, 110 bpm, and 130 bpm.

Figure 7:
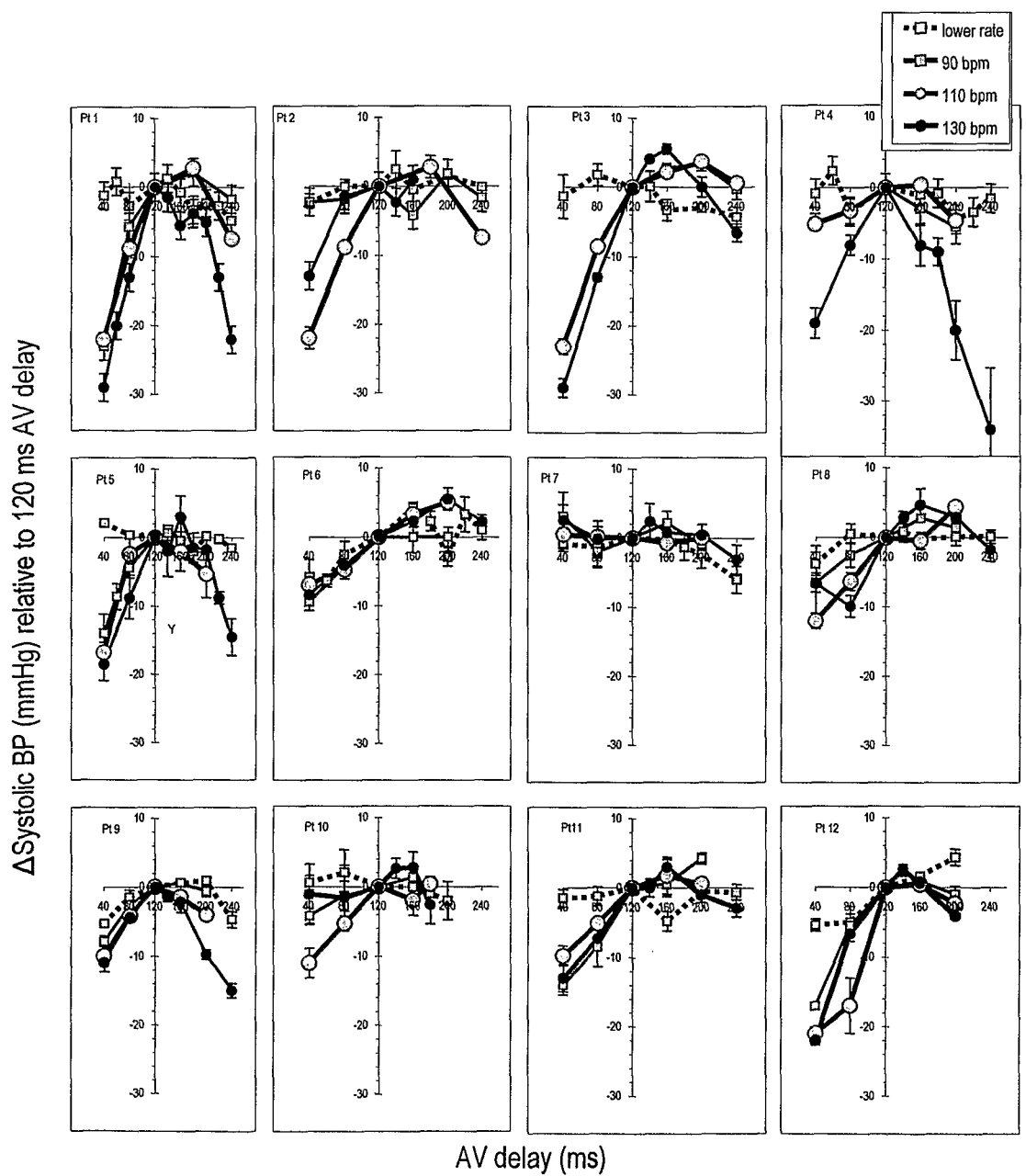

FIG. 7 shows a graph for each patient of Table 1. Each graph shows ΔBP (systolic blood pressure relative to systolic blood pressure at the reference AV delay of 120 ms) as the AV delay is varied between 40 and 240 ms. Furthermore, a curve is shown for the data at each of four heart rates: rest, 90 bpm, 110 bpm, and 130 bpm.

Figure 8:
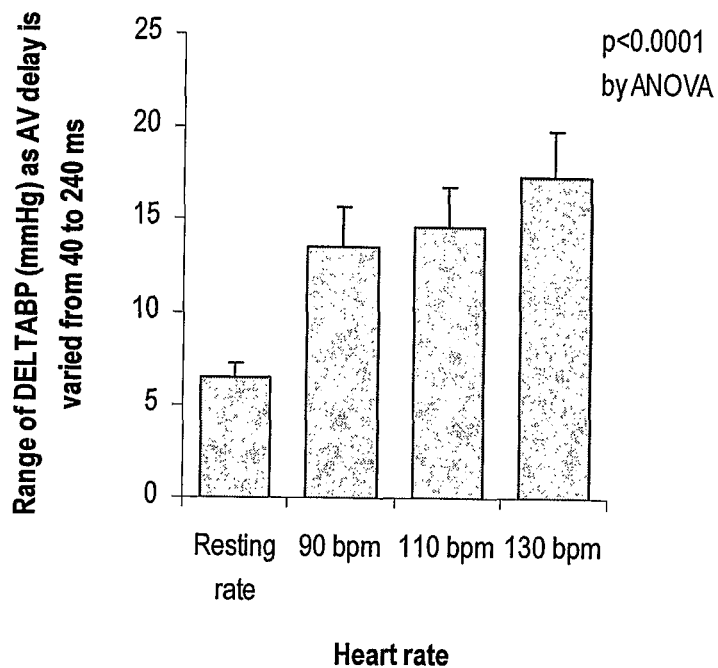

FIG. 8 is a graph showing the effect of AV delay optimization on systolic blood pressure at different heart rates. At each heart rate, the bar represents the average within-patient variation in ΔBP as AV delay is varied across a spectrum of values from 40 to 240 ms. The graph shows that, at higher heart rates, AV delay optimisation has a larger effect.

Figure 9:
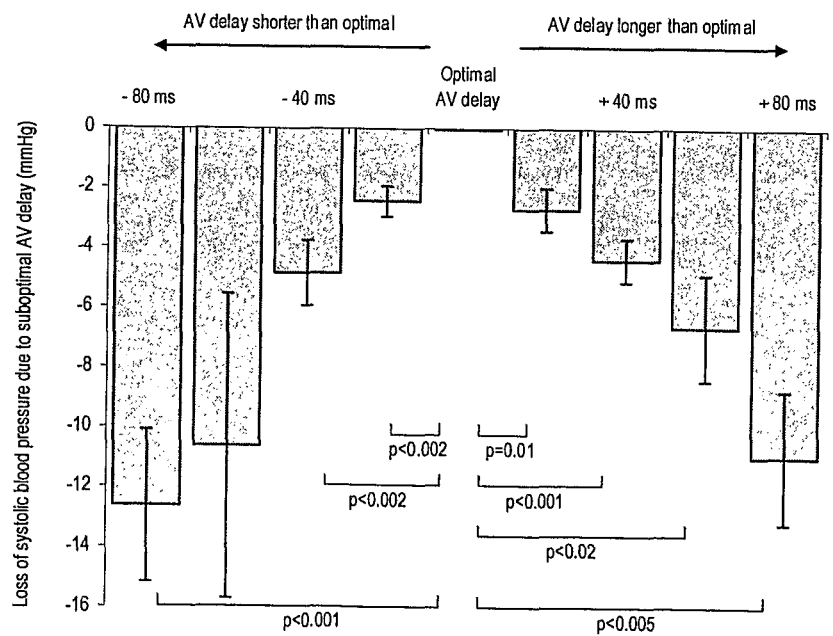

FIG. 9 is a graph showing the change in systolic blood pressure (averaged across all patients) as AV delay is moved away from its patient-individualized optimum. The statistically significant differences from optimal are labelled.

Figure 10:
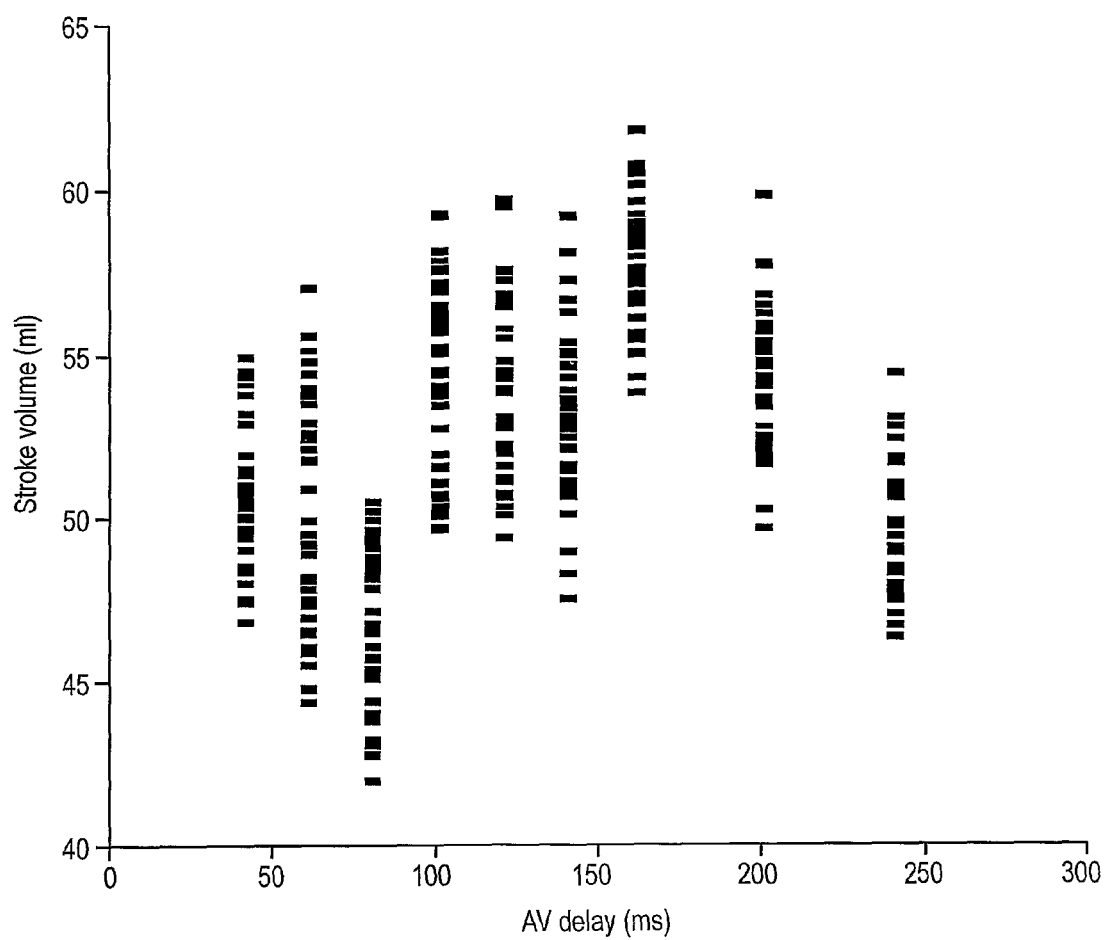

FIG. 10 shows echocardiographic stroke volume data for AV delays between 40 ms and 240 ms in patient 3 of Table 1 at a heart rate of 130 bpm.

Figure 11:
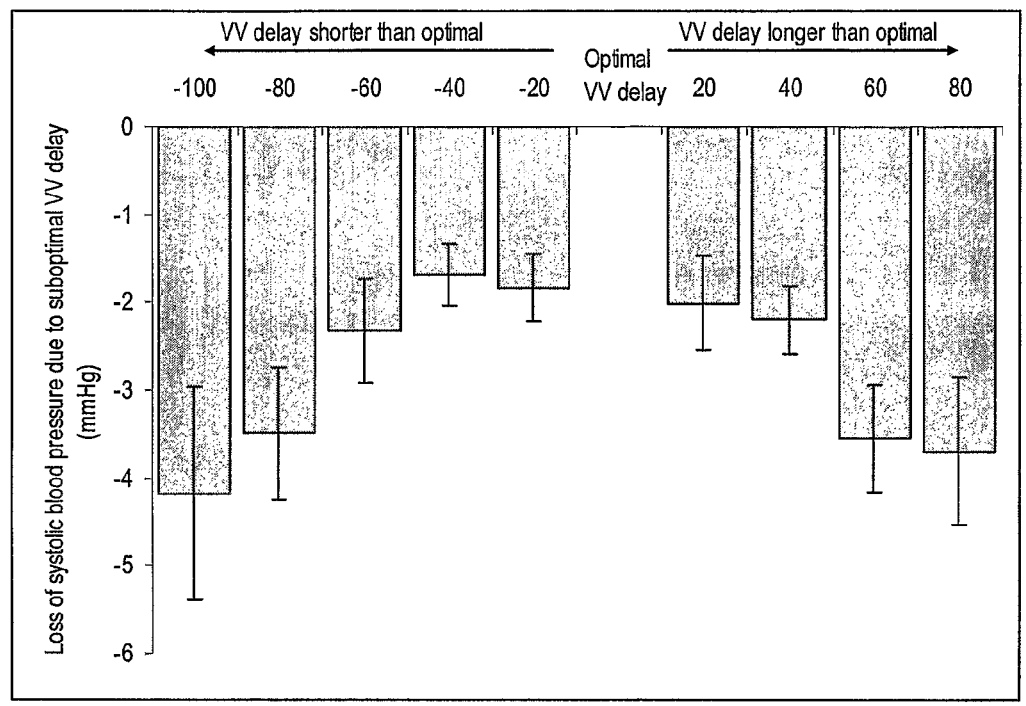

FIG. 11 is a graph showing the change in systolic blood pressure (averaged across 15 patients) as VV delay is moved away from its patient-individualized optimum. The statistically significant differences from optimal are labelled.

Figures 12A, 12B:
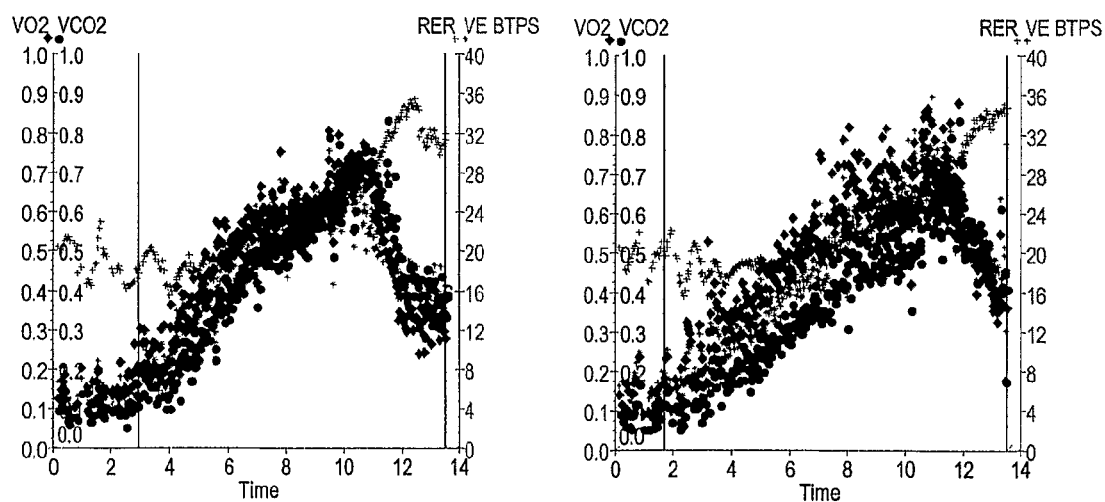

FIGS. 12 *a* and *b* are graphs showing the peak oxygen uptake (peak VO2) of patients whose pacemakers had been optimised using conventional echocardiographic methods (a) or using the methods of an embodiment of the present invention (b).

Figure 1:
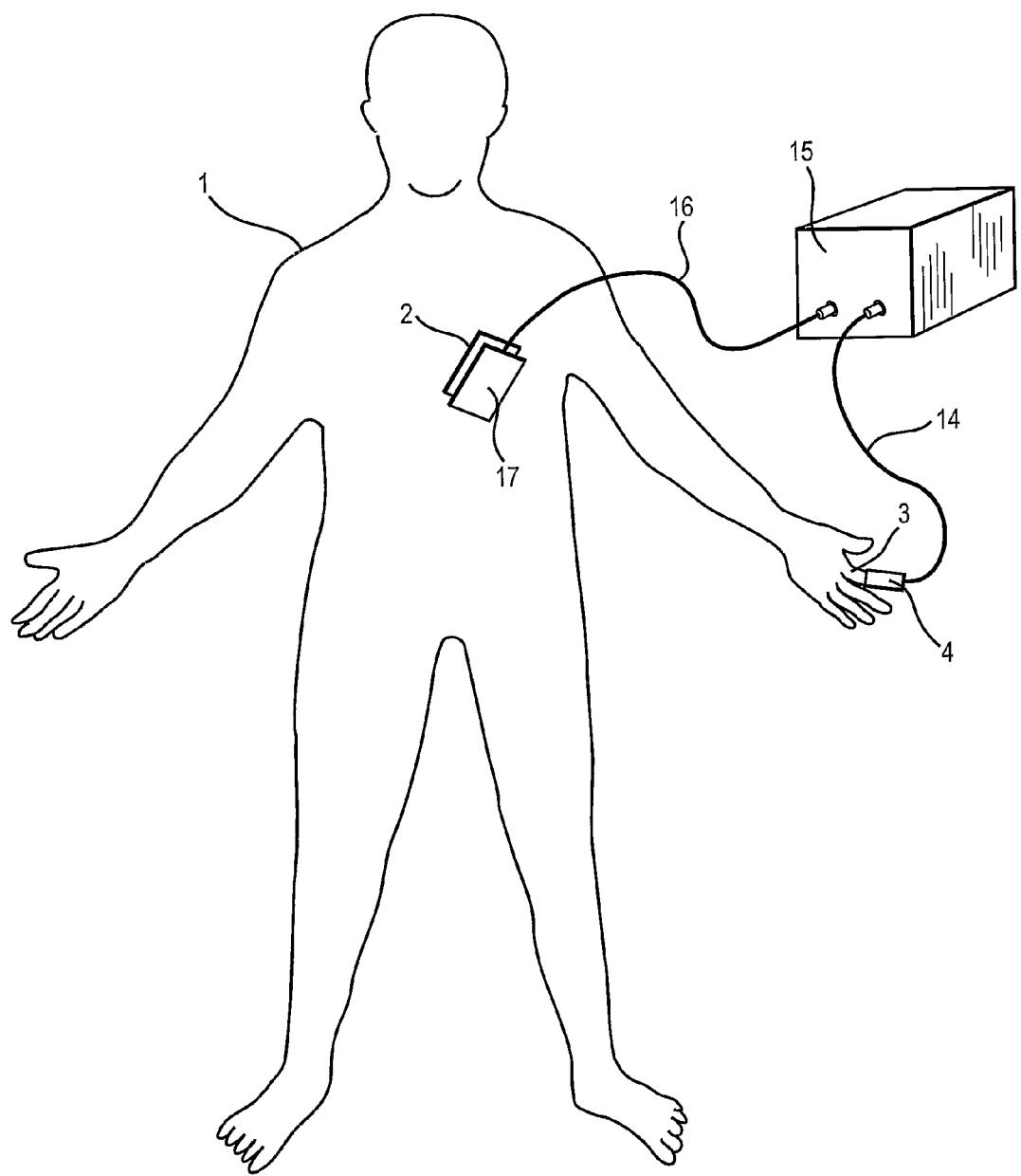
FIG. 1 is a schematic view of a pacemaker programming apparatus in accordance with one embodiment of the present invention.

Referring to FIG. 1, a pacemaker optimization session is shown in which a patient 1 previously fitted with an implanted atriobiventricular pacemaker 2 has, attached to his index finger 3, a finapres 4.

Figure 2:
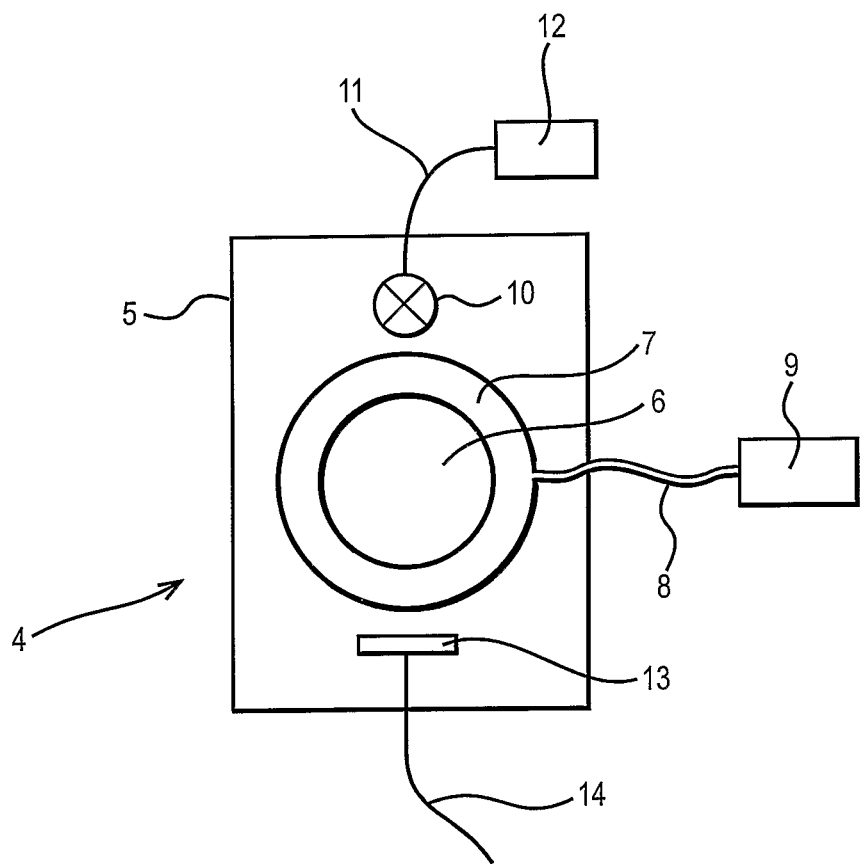
FIG. 2 is a schematic, cross-sectional view of a portion of a pacemaker programming apparatus in accordance with an embodiment of the present invention.

A finapres is a device which continuously monitors blood pressure. Finapres is an acronym for FINger Arterial PRESsure. Finapres devices are known in the art from, for example, NL-A-8105381 and CS-A-272057. In order to understand the workings of the finapres 4, reference will now be made to FIG. 2.

The finapres 4 comprises a housing 5 in which a substantially cylindrical aperture 6 is provided. The aperture 6 is adapted to receive the index finger of a human being. In other embodiments, the aperture 6 is adapted to receive a finger other than the index finger or is adapted to receive another body extremity. Around the interior of the aperture 6 there is an annular cuff 7, which is inflatable via a pipe 8 which leads from a pump 9.

Above the aperture 6 is provided a light source 10 which may, for example, be a light emitting diode. The light source 10 is powered, via a wire 11, by a power source 12.

Below the aperture 6, and thus opposite from the light source 10, is provided a light sensor 13. The light sensor 13 generates an electrical signal in response to the light from the light source 10 which is incident upon it. The signal is passed down the transmission wire 14, which leads from the light source 13.

Referring again to FIG. 1, the transmission wire 14 leads to a processor 15 which is programmed to process the signal from the light sensor 13, in order to generate a pacemaker programming signal in a manner which will be described in greater detail below.

Leading from the processor 15 is a communication wire 16, which extends to a transmitter 17 located on the body of the patient 1, adjacent the pacemaker 2. The transmitter 17 transmits the pacemaker programming signal, to the pacemaker 2 transcutaneously by magnetic induction. In some embodiments, data is also transmitted from the pacemaker 2 to the transmitter 17 and then via the communication wire 16 to the processor 15. For example, in some embodiments, data concerning the heart beat of the patient 1 is sent from the pacemaker 2 to the processor 15.

The arrangement permits digital photoplethymography to be used to optimize the programming of the pacemaker 2.

In use, the finapres 4 continuously measures the blood pressure of the patient 1 as will now be described. The annular cuff 7 is inflated about the index finger 3 of the patient 1 so as to constrict the finger 3. In the meantime, the light sensor 13 detects the light from the light source 10. The index finger 3 of the patient 1 interposes between the light source 10 and the light sensor 13 and intercepts the light from the light source 10. In particular, the index finger 3 absorbs or disperses the light due to the red blood corpuscles in the blood vessels of the finger, primarily the two arteries.

As the annular cuff 7 progressively constricts the index finger 3 of the patient 1, the amount of blood perfusing the index finger 3 is reduced and thus the amount of light reaching the light sensor 13 increases because there are fewer red blood corpuscles to intercept the light. When the pressure provided by the annular cuff 7 exceeds the intra-arterial pressure then the blood vessels in the index finger 3 are collapsed and the light received by the light sensor 13 is at its maximum.

By varying the pumping activity of the pump 9, the pressure in the annular cuff 7 is adjusted so that it is between the maximum (i.e. systolic) and the minimum (i.e. diastolic) intra-arterial blood pressure so that during each cardiac cycle the blood vessels of the index FIG. 3 of the patient 1 are collapsed and opened.

During the cardiac cycle, the light sensor 13 thus detects a maximum level of light at diastole and a minimum level of light at systole. Moreover, it is observed that there is an intermediate plateauing of the light detected, over time, between the maximum and minimum levels of light detected, which represents the time at which the artery has just opened and thus the pressure at which the intra-arterial blood pressure is substantially the same as the pressure in the annular cuff 7. Thus the signal generated by the light sensor 13 contains information from which the blood pressure of an individual can be determined.

Although the finapres 4 is not very accurate at determining the absolute blood pressure of a patient 1, it does have several advantages in this invention. Firstly, it gives much better temporal resolution than a sphygmomanometer with an arm band cuff, because there is continuous measurement of blood pressure, with the opportunity to sample not only systolic blood pressure and diastolic blood pressure but also true mean blood pressure, rate of change of pressure, estimated stroke volume, estimated cardiac output, and other features of the blood pressure that cannot be obtained from the systolic and diastolic values alone. Thus the finapres 4 is capable of providing a signal from which a range of haemodynamic measures and not just blood pressure of the patient 1 can be determined. Secondly, since a sample of the blood pressure is taken once per heartbeat instead of once every 30 seconds or so, the values can be averaged to give a very reliable indication of the changes in blood pressure (that is to say the relative blood pressure of the individual over time rather than the absolute blood pressure of the individual). Thirdly, unlike a sphygmomanometer with an armband cuff, it is possible to determine the blood pressure very quickly, instead of having to wait for an inflate-deflate cycle of the armband cuff. This allows the immediate effect of a change of a setting of a pacemaker attribute to be measured. Fourthly, unlike invasive arterial blood pressure determination, the finapres is non-invasive and so blood pressure monitoring can be carried out without excess risk to the patient 1 and requires considerably less technical skill on the part of the operator. Fifthly, unlike echocardiographic measures, the finapres 4 provides a clear signal which is highly amenable to direct interpretation by a processor, without requiring the skill of an experienced human operator. Furthermore, a human operator is not required to keep an echocardiogram probe in place.

The signal from the finapres 4 is sent to the processor 15 via the transmission wire 14. The processor 15 determines the blood pressure of the patient 1, or, more importantly, an arbitrary standard blood pressure for the patient 1 in a reference state. In this embodiment, the reference state is with the heart rate, AV delay and VV delay of the biventricular pacemaker 2 set to their factory settings.

The processor 15 then sends a command via the communication wire 16 to the transmitter 17 in order to adjust the setting of one of the attributes (i.e. one of the heart rate, the AV delay or the VV delay) of the pacemaker 2. Normally, however, it will be either the AV delay or VV delay because the heart rate is set automatically in response to the heart's natural rate.

In this test state, with the attribute adjusted to a different setting, the blood pressure of the patient is determined by the processor 15 and compared with the blood pressure measured in the reference state.

This process may then be repeated several times, each time adjusting the setting of an attribute of the biventricular pacemaker 2; determining the blood pressure of the patient 1; and recording the attribute setting and the resulting blood pressure.

Subsequently, the processor compares the blood pressure of the patient 1 in each of the states, selects the optimum blood pressure and records the setting of the attribute which results in the optimum blood pressure. It then sends a pacemaker programming signal, via the communication wire 16 and the transmitter 17 to set the attribute of the biventricular pacemaker 2 to the optimum setting.

It is to be appreciated that, in the above described embodiments, the reference to a single processor 15 is somewhat arbitrary since, in practice, the finapres 4 may incorporate its own processor for continuously determining the blood pressure of the patient 1 and that information is then converged to the processor 15 for the subsequent processing steps in order to optimise the pacemaker settings. However, for the purposes of this description, only a single processor is described.

In the above-described embodiment the attributes of the pacemaker were at their factory settings in the reference state. However, in other embodiments, the attributes have other settings in the reference state. In some embodiments, the attributes are adjusted to other constant settings such as an AV delay of 120 ms and a VV delay of 0 ms in the reference state. In some other embodiments the settings of the attributes are adjusted by a human operator at the beginning of the optimisation session in order to define the reference state. In some alternative embodiments, the reference state is defined as whatever the settings of the attributes of the pacemaker are when the patient arrives for the optimisation session. Thus as the patient has successive pacemaker optimisation sessions, his pacemaker is reoptimised starting from the previous optimal settings.

In some embodiments, the process is then repeated with a second attribute. For example, the process is first carried out to set the pacemaker to the optimum AV delay and, subsequently, the optimum VV delay of the pacemaker 2 is determined and set at its optimum setting.

In some preferred embodiments, the optimum setting for a particular attribute is the setting which results in the highest haemodynamic measure, especially the highest blood pressure, of the patient 1. In order to explain the reason for this, it is firstly to be appreciated that high blood pressure both damages the circulation of a patient and reflects an improved ability of the heart of the patient to pump. In the general "healthy" population of developed countries (almost all of whom have good systolic function) damage to the circulation is the overwhelmingly important effect of high blood pressure. Thus in the general population, higher blood pressure is almost always linked to a poorer prognosis. However, in patients with advanced heart failure, high blood pressure is overwhelmingly associated with the improvement of impaired pump function so that higher blood pressure is, paradoxically, a good prognostic sign. This has been shown both in population based studies[14,15,16,17] and clinical trials[18]. Therefore, in preferred embodiments, the optimum setting of an attribute is the setting that results in the maximum haemodynamic measure for a patient.

In preferred embodiments, the optimum setting for the attributes of the pacemaker 2 are determined while the patient 1 has a raised heart rate. This is achieved by the patient undertaking exercise (e.g. jogging on a treadmill) in order to increase the heart rate while the above described process is carried out. It is to be appreciated that the use of the finapres 4 to determine a haemodynamic measure is relatively unobtrusive and therefore permits the patient 1 to exercise even while the pacemaker programming takes place. This is to be contrasted with the prior art approaches where it is difficult, if not impossible, for the patient 1 to carry out any exercise during invasive blood pressure monitoring or echocardiography.

The advantage of determining the optimum settings of attributes of the pacemaker 2 when the patient has a raised heart rate is that it has been found by the present inventors that it is only when the heart rate is increased that almost all patients show a clear optimal setting of the biventricular pacemaker. In contrast, at resting heart rates, for most patients the settings of the attributes of the pacemaker are relatively unimportant.

For example, when the change in a haemodynamic measure of a patient is plotted on the Y axis of a graph against the change in the setting of an attribute (e.g. AV delay) on the X axis then this data typically forms a parabola. However, only at higher heart rates of a patient is the parabola sufficiently curved to be visible. The vertex of the parabola identifies the optimal setting of the attribute (i.e. the greatest increase in the haemodynamic measure).

Therefore, if a patient has a typical resting heart rate of 70 bpm then, in one embodiment, then the heart rate of the patient is raised to 110 beats per minute, at which heart rate the optimum settings for the attributes of the pacemaker are determined.

In some variations of this embodiment, the optimum settings of the attributes of the pacemaker are determined at more than one raised heart rate (for example at 110 bpm and 130 bpm when resting heart rate was 70 bpm). The processor 15 then interpolates (either linearly or otherwise) to determine the optimal settings of the attributes of the biventricular pacemaker at heart rates between those at which the optimum settings were determined. In these variants, the pacemaker programming signal contains information providing the pacemaker with the optimum settings of the attribute at a range of heart rates so that the pacemaker 2 can vary the settings of the attributes as the heart rate of the patient changes.

In preferred embodiments, a limited number of actually measured values are used to interpolate between the measured settings to identify an optimal setting of an attribute (i.e. that which is interpolated to give the highest value of the haemodynamic measure). For example, it has been found that the pattern of the haemodymamic measure typically resembles a parabola. It is therefore possible to fit the data points automatically to a parabola according to the following formula:

$$h = as^2 + bs + c$$

wherein h=haemodynamic measure and s=setting.

The optimal value of the "setting" is then interpolated using the following formula:

$$e = -\frac{b}{2a}$$

wherein e=estimated optimal setting.

Although not all conceivable settings may be achievable with any given individual pacemaker (due to restrictions of the device, which may, for example, allow AV delay to be set only in multiples of 10 ms), with this approach it is possible to identify rapidly the interpolated optimal setting from a few measurements, and then to select the closest achievable setting. Higher-order polynomial curve fits, or sinusoidal approximations, or other curve fits, are applied in alternative embodiments.

In some alternative variants, the optimum setting of the attributes is determined at more than one raised heart rate and then a best fit setting of the attributes is selected so that, even if the settings are not changed as the heart rate is changed, the settings of the attributes are such as to be closest to the optimum settings no matter what the heart rate is.

The present inventors have also found that there is a natural, random drift in the blood pressure of a patient over time. Consequently, it is undesirable to measure the absolute blood pressure values of a patient at each possible setting of the attributes of pacemaker because the physiological noise caused by the drift in blood pressure obscures the optimum settings. Accordingly, in some embodiments, the determining of the optimum settings of the attributes of the pacemaker is carried out as follows, relying on a different haemodynamic measure.

The processor 15 sets the pacemaker 2 (via the transmission wire 16 and the transmitter 17) to a reference setting of one attribute for a test period lasting a predetermined number of heart beats (e.g. 10 heartbeats) during which time the blood pressure of the patient is measured. After the test period, the setting of the attribute is changed to a first test setting and the blood pressure of the patient is measured for a second test period. The pacemaker is then returned to the reference setting for a third test period during which time the blood pressure of the patient is determined. Subsequently, the attribute of the pacemaker is adjusted to a second test setting for another test period during which time the blood pressure of the patient is measured. This process is repeated, with the setting of the attributes of the pacemaker alternating between the reference setting and a variety of test settings. For example, the reference setting may represent an AV delay of 120 ms and the test settings range from 40 to 240 ms in steps of 40 ms.

The advantage of this embodiment is that the blood pressure at each test setting can be compared with the blood pressure at the immediately preceding, and subsequent, reference setting thus revealing the change in blood pressure achieved or, in other words, the "relative benefit". This eliminates the effect of any gradual trends in blood pressure. For example, if the blood pressure is trending downwards over a period of one minute, the average of the 10 heart beat test period when the pacemaker is in a test setting will be similar to the average of the preceding and succeeding test period with the pacemaker at the reference setting. Thus in this embodiment, the haemodynamic measure is the relative change in blood pressure between a test setting and the preceding and subsequent reference settings.

Moreover, the alternating nature of the transitions assists in eliminating the effects of slow trends in blood pressure. For example, consider a situation where a transition in AV delay from 120→160 ms causes an increase in blood pressure of 6 mmHg, but blood pressure is also slowly trending downwards over a few minutes at a rate sufficient to create a downward artefact of 2 mmHg during the measurement period of a transition. During a "forward" transition from 120→160 ms, the measured DELTA BP will be 4 mmHg (i.e. 6-2 mmHg, an underestimate) but during a subsequent "reverse" transition from 160→120 ms, the measured DELTA BP will be −8 mmHg (−6-2 mmHg, an overestimate of the magnitude). The average DELTA BP for the 120→160 transition is calculated from all the measured DELTA BP values of the forward transitions and the reverse transitions (whose DELTA BP values will of course have to be reversed in sign in order to be comparable). Thus the contributions of the two DELTA BP measurements just considered will be 4 and 8, whose average value is 6 (i.e. the error induced by the slow downward drift has cancelled out). Therefore a steady gradual trend will not affect the averaged measure of change in haemodynamic measure in this embodiment.

In some embodiments, the setting of the attributes of the pacemaker is alternated more than once between the reference setting and each test setting. This permits an averaging of the data received to take place to reduce the effect of any artefacts in the data. In some versions of these embodiments, the number of alternations is predetermined. For example, in one embodiment, there are three alternations which results in six transitions between the reference setting and each test setting. In other versions of these embodiments, the number of alternations is varied in response to the result of a comparison of the haemodynamic measure over successive replicated alternations. In one embodiment, for example, when the haemodynamic measure is substantially different between successive alternations then the number of alternations is increased from a standard but if the haemodynamic measure is substantially the same between successive alternations then the number of alternations is decreased from the standard.

In alternative embodiments, the setting of an attribute of the pacemaker is maintained for a test period of, for example, 10 heart beats but instead of alternating between a test setting and the reference setting, the pacemaker is randomly moved between test settings of the attribute. The advantage of this embodiment is that more of the available time of the optimization session is spent investigating the test settings of the attribute.

It is to be appreciated that a biventricular pacemaker typically has three settings: the heart rate, the AV delay and the VV delay and that usually the optimum setting of the AV delay and the VV delay will need to be determined. In some embodiments this is achieved by carrying out the process only in relation to one attribute (e.g. AV delay) and then by repeating the process varying the other attribute (e.g. VV delay) so that the two optimal settings are determined independently of one another. In alternative embodiments, both attributes are varied simultaneously in order to determine the optimum setting for both attributes. For example, in one embodiment, a reference state is defined with particular settings of the AV delay and VV delay. In the optimization session, the pacemaker is alternated between test periods in the reference state and test periods in which the settings of the AV delay and the VV delay are adjusted to various test settings. In each successive test setting the AV delay and the VV delay are different from the previous test setting.

In the above described embodiments, the pacemaker is an atriobiventricular pacemaker. However, in other embodiments, the pacemaker is a biventricular pacemaker with two ventricular leads in which only the setting of the VV delay is optimized or is a standard dual chamber pacemaker in which only the setting of the AV delay is optimized. In further embodiments, the pacemaker has a greater number of leads than 3, for example if multiple leads are placed in the atria and/or ventricles.

Reference will now be made to the operation of the processor 15. In order to operate as described above, the processor 15 is programmed with a computer program in order to adjust the pacemaker 2 during testing, analyse the blood pressure indication signal from the finapres 4 and generate a pacemaker programming signal with which to program the pacemaker 2. The computer program comprises an attribute selection module, which selects an attribute and instructs a testing module to operate on the selected attribute.

The testing module contains code for receiving the blood pressure indication signal while the setting of the selected attribute of the pacemaker 2 is adjusted. More specifically, the testing module comprises a first module for selecting a setting of the attribute; a second module for receiving the blood pressure indication signal and a third module for recording the setting of the attribute and the respective blood pressure indication signal which resulted at that setting of the attribute. The testing module also comprises a fourth module which loops the activity of the first, second and third modules. In some embodiments, the fourth module instructs the first module to select the same setting of the attribute at every other repeat of the loop. That is to say, alternate repeats have the same setting. In other embodiments the fourth module instructs the first module to select a different setting of the attribute at every repeat of the loop.

The computer program also comprises a determination module which contains code for determining, from the series of blood pressure indication signals recorded by the third module of the testing module, the change in blood pressure of the individual at each setting of the attribute.

In some embodiments, the computer program further comprises a heart beat detection module, which contains code for receiving a signal indicative of the heart rate of the individual. This signal is received from the pacemaker 2, in embodiments in which the pacemaker 2 transmits data via the transmitter 17 to the processor 15. In other embodiments, the pulse of the individual is detected independently. The heart beat detection module instructs the first, second and third modules to carry out each loop of their activity for a predetermined number of heart beats, such as 10 heart beats.

The computer program also contains a setting selection module which contains code for comparing the data generated by the determination module and selecting a setting of the attribute by choosing the setting which results in the optimum blood pressure, preferably the setting which results in the greatest increase in blood pressure.

The computer program also comprises a programming module which contains code for generating a pacemaker programming signal which encodes the setting of the attribute which has been selected by the setting selection module for transmission to the pacemaker 2, via the communication wire 16 and the transmitter 17. This module thus permanently (or, at least, semi-permanently) programs the pacemaker 2 with the optimum settings.

In some embodiments, the attribute selection module also contains code for instructing the first module to operate on a second attribute, once the activity in relation to the first attribute has been completed. Alternatively, the first module also contains code for selecting a setting of a second attribute and the third module contains a code for recording the combination of settings of the first and second attributes together with the blood pressure indication signal which results from that combination. Thus the optimum settings of the first and second attributes are determined simultaneously.

In these embodiments, where the optimum settings of two attributes are determined, the determination module also contains code for determining the change in blood pressure of the individual during adjustment of the setting of the second attribute. Similarly, the setting selection module and the programming module are adapted also to select the optimum setting of the second attribute and generate the pacemaker programming signal which encodes the selected setting of the second attribute, respectively.

As previously explained, in preferred embodiments, the computer program is adapted to operate when the patient 1 has a raised heart rate.

Once a pacemaker 2 has been programmed with the optimum settings, the patient is free to go about his normal activities, with the pacemaker acting according to the programmed settings of the attributes. It is preferred that the optimization is repeated every one to two years and also after any change in clinical status of the patient such as a myocardial infarction.

In the above described embodiments of the invention, the optimization of the pacemaker is achieved generally by determining either the absolute blood pressure of the patient at different settings of an attribute and selecting the setting resulting in the highest absolute blood pressure or by determining the relative increase in blood pressure of the patient at different settings and selecting the setting resulting in the greatest increase in blood pressure. However, it should be understood that, in other embodiments of the present invention, different haemodynamic measures are used. For example, in some embodiments, the haemodynamic measure is the absolute blood pressure of a patient at more than one point in time or the change in blood pressure of a patient over a period of time or even another computation over time. Furthermore, the haemodynamic measure may relate to a particular aspect of the blood pressure indication signal. The aspect of the blood pressure indication signal addressed may be the systolic pressure, diastolic pressure, mean pressure, pulse pressure, rate of change of pressure, peak rate of change of pressure, or any other aspect of blood pressure which can show a significant improvement when biventricular pacing is applied. Moreover, the haemodynamic measure may be something other than a blood pressure value per se. For example, it may be a calculation, from the blood pressure signal, of an estimated stroke volume or cardiac output. Once the haemodynamic measure is determined at the required numbers of settings, the optimum haemodynamic measure is ascertained and the setting of the attribute(s) which resulted in the optimum haemodynamic measure is selected.

It is to be appreciated that, although the above described embodiments of the present invention comprise a finapres 4, the finapres 4 is not an essential feature of the invention. For example, in other embodiments of the invention a different type of non-invasive blood pressure measuring device is provided instead of the finapres 4, such as a pulse oximeter or a bio-impedance monitor. Alternatively, an invasive blood pressure measuring device is used such as a device (e.g. an accelerometer or Doppler beam) included in the implanted pacemaker system.

In some embodiments, in addition to the monitoring of blood pressure using the finapres 4 (or another blood pressure measuring device), a device is also provided which monitors the phase of respiration of the individual and generates a respiration signal. In addition, a device is provided which monitors the body movements of the individual. In some embodiments, the device is a strain gauge. The output from these devices is transmitted to the processor 15 and the processor 15 is programmed to take account of the phase of respiration and any detected body movements so as to remove any artefacts in the measurement of the blood pressure that might be caused by such activity. The processor achieves this by comparing the haemodynamic signal with the respiration signal and determining the transfer function between the two signals during a stable period when the settings of the attributes are not altered. During a test period, the processor uses this transfer function together with the observed respiration signal during a transition in order to predict the effect of respiration during the transition and subtract the predicted respiratory effect from the haemodynamic signal.

In the above-described embodiments, a test period lasts a predetermined number of heart beats. However, this is not an essential feature of the invention and in other embodiments, the length of test periods is determined differently. For example, in some embodiments, the respiratory cycle of the individual is monitored and the test period lasts for a length of time related to the respiratory cycle. For example, in one embodiment, the test period lasts for a complete respiratory cycle.

In some embodiments, during the period of time of the first few heart beats of an individual in each test period, the blood pressure or other haemodynamic measure of the patient is ignored. It is particularly preferred that during the length of period of time during the first two heart beats of the individual in each test period, the blood pressure or other haemodynamic measure is ignored. The reason for this is that the immediate effect of the transition from one setting of an attribute to another results, in many patients, in an artefact lasting one or two heart beats, which is larger than the actual eventual signal. Therefore, by omitting the inclusion of any data taken during this period of time, the artefact is not included in the analysis. In some embodiments, the length of time during which data is ignored is fewer than five heart beats of the individual.

EXAMPLES

Methods

Subjects

Twelve outpatients who had biventricular pacemakers or biventricular defibrillators in situ which had been implanted on standard clinical grounds (NYHA III or IV heart failure, QRS>120 ms, maximal medical therapy) were enrolled in the examples of this study. The pacemaker had been inserted between 1 month and 2 years previously. The VV delay was not altered during the study and was set to 4 ms in all patients. Patients gave informed consent for this study which was approved by the local Ethical committee. The patient characteristics are summarized in Table 1.

TABLE 1

| Patient | Age | Sex | Cause of Heart failure | NYHA | LVEF % | LVEDD | LVESD | AV optimization by Echo (LV inflow) |
|---|---|---|---|---|---|---|---|---|
| Pt 1 | 77 | M | IHD | II | 40 | 6.8 | 5.2 | 140 ms |
| Pt 2 | 50 | M | IHD | II | 26 | 7.5 | 6.9 | 120 ms |
| Pt 3 | 70 | F | IHD | II | 52 | 5.2 | 4 | 110 ms |
| Pt 4 | 78 | F | IHD | II | 38 | 5 | 3.9 | 110 ms |
| Pt 5 | 62 | M | DCM | III | 55 | 4.4 | 3.4 | 120 ms |
| Pt 6 | 69 | M | IHD | III | 37 | 7.3 | 6.1 | 140 |
| Pt 7 | 77 | M | IHD | II | 30 | 6.0 | 5.4 | 110 |
| Pt 8 | 77 | F | Alcohol | III | 25 | 7.29 | 6.0 | 110 ms |
| Pt 9 | 48 | M | DCM | III | 35 | 6.2 | 4.7 | 140 ms |
| Pt 10 | 57 | M | IHD | III | 20 | 9 | 7.5 | 105 ms |
| Pt 11 | 79 | M | IHD | III | 30 | 6.9 | 6.4 | 110 ms |
| Pt 12 | 60 | M | IHD | III | 26 | 6 | 5.4 | 140 ms |

Measurements

Data Acquisition

Non-invasive finger arterial pressure measurements were made using a Finapres model 2300 digital photoplethysmograph. This technique, which is further described in the detailed description, was developed by Peñá[28] and Wesseling[29] and may be summarized in that it uses a cuff, which is placed around the index finger, and a built-in photo-electric plethysmograph, in combination with a volume-clamp circuit that dynamically follows arterial pressure. This technique is a well-validated method of measuring instantaneous changes in blood pressure[30]. An ECG signal was also recorded. These signals were acquired via an analog-to-digital card (National Instruments, Austin, Tex.) using custom software developed in our laboratory[31] an analyzed off line with further custom software based on the Matlab platform (MathWorks, Natick, Mass.).

Example 1

Measurement of Relative Change in Blood Pressure Across Different AV Delays

The beat to beat pressure was recorded during adjustment of the AV delay of the subject's biventricular pacemaker. In order to minimize the effects of unavoidable spontaneous fluctuations in blood pressure, each AV delay was compared with a fixed AV delay. At the time of pacemaker reprogramming, there was a prompt change in arterial blood pressure (see FIG. 3). Over a period of minutes, spontaneous random trends and slow variations in blood pressure can make it difficult to identify precisely the increment related to pacemaker reprogramming. By taking the 10 beats immediately before a reprogramming and the 10 beats immediately afterwards, and calculating the difference in mean systolic blood pressure (ΔBP) for that single transition, an estimate of the relative blood pressure effect was made, minimizing both the short-term respiratory noise and the longer-term fluctuations. The transitions (see FIG. 4) were repeated, reversing the signs of ΔBP for reverse transitions, to obtain at least 6 replicate measurements for each ΔBP. These were combined to obtain, for each AV delay, a mean ΔBP along with the standard error of the mean, to give an estimate of precision.

Delta BP was measured in the manner described above for each AV delay (40 ms, 80 ms, 160 ms, 200 ms, 240 ms) as shown in FIG. 5.

Statistics

The ΔBP value was determined for each AV delay in relation to a reference AV delay (120 ms) by taking the mean of observed blood pressure changes from at least 6 individual transitions. ΔBP was plotted as a mean value and standard error of the mean (FIG. 5). Paired comparisons were made using Student's paired t test. Comparisons between multiple heart rates were made using repeated-measures ANOVA. Comparisons of proportions were made using Fisher's exact test. A p value of <0.05 was taken as statistically significant. The statistical package Statview 5.0 (SAS Institute Inc., Cary, N.C.) was used for analyses.

Effect of Biventricular Pacing

All twelve patients yielded readily analyzable data. As shown in FIG. 3, there was a prompt change in systolic blood pressure when the AV delay was changed. In three patients the longest AV delay tested was less than 240 ms, because of interactions with the defibrillator settings.

This example shows that systemic hemodynamic effects of changes in AV delay in patients with cardiac resynchronization were immediately detectable by continuous noninvasive hemodynamic monitoring.

A variety of hemodynamic improvements are recognized to occur acutely with resynchronization[1,6,7,11,12], and each is a potential guide for hemodynamic optimization. To reduce the effect of random variation, it is advantageous to take an average of multiple heartbeats. Multiple measurements (necessitating relatively long recordings) are safer to do if left ventricular catheterization is not involved. Thus arterial blood pressure can be used as an acute hemodynamic measure.

Example 2

The protocol was then repeated for other heart rates, by reprogramming the pacemaker's lower rate limit, yielding for each patient 4 separate curves (resting rate, 90, 110, 130 beats per minute). Measurements of relative change in blood pressure and statistics were calculated as in Example 1.

Effect of Altering AV Delay at Resting Heart Rate

Data for patient 3 is shown in FIG. 6 and individual data for each of the 12 patients is shown in FIG. 7. To allow for comparisons between patients, all blood pressures are expressed as relative (ΔBP) to the blood pressure obtained in that individual patient at a reference AV delay of 120 ms. Since 120 ms was the reference AV delay, each curve passes through a ΔBP of zero mmHg at an AV delay of 120 ms. The resting data is shown in the dotted curves of each panel.

At resting heart rate, as AV delay was varied over the range 40 to 240 ms, although there was detectable variation in systolic blood pressure, this variation was small. For each patient, the "range of ΔBP values across different AV delays" was calculated (see FIG. 5) at the resting heart rate. Over all 12 patients, at resting heart rate the range of ΔBP across different AV delays averaged 6.5 mmHg.

Effect of Altering AV Delay at Higher Heart Rates

In all 12 patients, alterations in AV delay had a more pronounced effect on BP at higher heart rates than at lower heart rates, as can be seen in FIG. 7. As the heart rate increased, the range of ΔBP across different AV delays became progressively wider in the group as a whole (p<0.0001 by ANOVA, FIG. 8) reaching 17.4 mmHg at 130 bpm. All 12/12 patients showed a clear hemodynamic optimum at higher heart rates, while only 3/12 showed this at resting heart rate (p<0.0005 by Fisher's exact test). Individual patients had different optimal AV delays (shortest 120 ms, longest 200 ms).

Therefore this example shows that the effects of adjusting AV delay were more profound at higher heart rates than at resting heart rate.

At lower heart rates, AV delay was observed to make a relatively small difference to systolic blood pressure. At higher heart rates, however, a more profound increment in blood pressure was recorded at optimal AV delays (ranging by 25 mmHg at 130 bpm). While not wishing to be bound by any particular explanation, it is thought that this observation may have a physiological explanation. Resynchronization has two important effects on myocardial activity. Firstly, it makes contraction more synchronous, increasing LV dp/dt[10], and therefore making for a more efficient systole. Secondly, more time becomes available for left ventricular filling. For many patients, at rest, this improvement in filling is not important, because filling time may already be sufficient. However, at higher heart rates, filling time may become a limiting factor, and optimization that improves filling time may therefore improve arterial blood pressure.

The consequences of non-optimal AV delay are visible as a significant loss of arterial blood pressure, which increases in magnitude as heart rate increases. Since many patients with heart failure report symptoms only on exertion, it is advantageous that optimization assessment of cardiac resynchronization is carried out at higher heart rates.

Example 3

In this example, the blood pressure of each patient was analysed as the AV delay was adjusted away from the optimum for the patient.

Effect of Non-Optimal AV Delay for Individual Patients

Blood pressure was observed to be progressively lower as AV delay was changed away from the individual patient's hemodynamic optimum. The average decline across all patients is shown in FIG. 9 for the heart rate of 130 bpm. Even a small alteration in AV delay of 20 ms causes a statistically significant decline (p<0.002 for AV delay 20 ms shorter than optimal, and p=0.01 for AV delay 20 ms longer than optimal).

Therefore, this example shows that even small changes in AV delay away from the optimum have a significant effect on arterial blood pressure.

The changes in blood pressure evinced by changes of 20 or 40 ms in AV delay away from optimal may seem superficially small, but even small differences in hemodynamic status are known to be associated with significant absolute differences in outcome in patients with chronic heart failure. For example, 1 mmHg less blood pressure in a patient with chronic heart failure is known to be associated with a relative increase in mortality hazard of approximately 4% higher mortality[15]. This indicates that apparently small differences in blood pressure are not negligible.

Example 4

Echocardiography

Stroke volume was calculated from the velocity time integral of the pulse wave Doppler recorded in the aortic outflow tract, in combination with a cross sectional area determined from LVOT dimension. Multiple beats were recorded and the average velocity time integral over at least 30 beats was determined using custom signal averaging software. The AV delay providing the maximum cardiac output was determined at a heart rate of 130 bpm.

AV optimization was also performed using the echo method that provided the longest diastolic filling time without interruption of the a wave, maximizing LV inflow time as previously described by Ritter[19,20,21]. In accordance with standard clinical practice this was done at resting heart rates.
Comparison with Echocardiographic Measurements The velocity-time integral (VTI) of Doppler left ventricular outflow tract velocities was measured at AV delays between 40 at 240 ms in each patient at a heart rate of 130 bpm (example shown in FIG. 10). In 6 patients, the echocardiographically optimal AV delay (the one with the greatest VTI) was the same as the optimal AV delay by continuous noninvasive hemodynamics. In five of the remaining 6, the optimal AV delays by the two approaches were within 40 ms of each other. The mean absolute difference in optimum AV delays between methods was 18 (standard error 6) ms.

Patients also underwent selection of theoretically optimal AV delay by the left ventricular inflow echocardiographic method of Ritter[19,20,21]. The mean absolute difference in optimal AV delay between the LV inflow method and the continuous hemodynamics method was 36 (standard error 6) ms.

The arterial blood pressure optimum was observed broadly to correspond with stroke volume optimum as assessed by Doppler echo of the aortic outflow tract. Although this approximate concordance is some evidence that the optima are equivalent, the agreement between methods will always be limited by inherent noise in the measurement of each. A "signal to noise ratio" can be calculated as the difference between measurements at two AV delays, divided by the average of the standard errors at the two AV delays. Signal-to-noise ratio was higher (averaging 5.5 across all 12 patients) for the blood pressure assessments than for the echocardiographic measurements (averaging 2.6 across all 12 patients).

For the purposes of optimization, echocardiographic VTI measures are handicapped by the requirement for a skilled operator, maintenance of constant position of probe and patient for a long study, and quantification of the Doppler signal into velocities. This more than two-fold advantage in signal-to-noise ratio means firstly that digital photoplethysmography can identify optima more easily, and secondly that it may be difficult to validate by comparison to echocardiographic VTI.

Example 5

The acute blood pressure of fifteen patients implanted with pacemakers was measured as the VV delay was shortened and lengthened from its haemodynamic optimum. The results are plotted in FIG. 11, which shows the fall in acute blood pressure as the VV delay moves away from the haemodynamic optimum.

Example 6

With prior informed consent, the programming of the pacemakers of three patients was optimised using the method of the present invention and using a conventional echocardiographic method. The patients' pacemakers were optimised by each of the two methods in turn (in a random, blind order) and the patients underwent cardiopulmonary exercise testing with each of the two settings. The exercise test was conducted and analysed by operators blind to the optimised method. The peak oxygen uptake (peak VO2) was measured and the results are shown in Table 2 and in FIG. 12.

The data demonstrate the type of difference in exercise capacity that is achievable using the method of the present invention compared with conventional echocardiographic methods.

TABLE 2

| | Peak exercise oxygen uptake (ml/kg/min) | |
|---|---|---|
| | Optimized by echocardiography | Optimized by method of present invention |
| Patient 1 | 8.9 | 10.1 |
| Patient 2 | 15.7 | 18.3 |
| Patient 3 | 21.5 | 22.2 |

REFERENCES

[1] Kass D A, Chen C H, Curry C, et al. Improved left Ventricular Mechanics From Acute VDD Pacing in Patients with Dilated Cardiomyopathy and Ventricular Conduction Delay. *Circulation.* 1999; 99: 1567-1573.

[2] Auricchio A, Ding J, Spinelli J C, et al. Cardiac resynchronization therapy restores optimal atrioventricular mechanical timing in heart failure patients with ventricular conduction delay. *J Am Coll Cardiol.* 2002; 108:929-932.

[3] Auricchio A, Abraham W T. Cardiac resynchronization therapy: Current state of the Art cost versus benefit. *Circulation* 2004; 109:300-307.

[4] Kerwin W, Botvinick E, O'Connell J W, et al. Ventricular Contraction Abnormalities in Dilated Cardiomyopathy: Effect of Biventricular Pacing to Correct Interventricular Dyssynchrony. *J Am Coil Cardiol.* 2000; 35:1221-7.

[5] Auricchio A, Stellbrink C, Block M, et al. Effect of pacing chamber and atrioventricular delay on acute systolic function of paced patients with congestive heart failure. *Circulation* 1999; 99:2993-3001.

[6] Yu Y, Kramer A, Spinelli J, Ding J, Hoersch W and Auricchio A. Biventricular mechanical asynchrony predicts hemodynamic effect of uni- and biventricular pacing. *Am J Physiol Heart Circ Physiol.* 285; 2003: H2788-H2796.

[7] Butter C D, Auricchio A, Stellbrink C, et al. Effect of resynchronization therapy stimulation site on the systolic function of heart failure patients. *Circulation*. 2001; 104: 3026-3029.

[8] Butter C D, Stellbrink C, Schlegl M, et al. Long term effect of cardiac resynchronisation therapy on basal hemodynamics. *Heart Rhythm;* 2004: Vol 1 No 1 581.

[9] Breithardt O, Stellbrink C, Franke A, et al. Acute effects of cardiac resynchronization therapy on left ventricular Doppler indices in patients with congestive heart failure. *Am Heart J.* 2002; 143:34-44.

[10] Van Gelder B M, Bracke F A, Meijer A, et al. Effect of Optimizing the VV Interval on Left Ventricular Contractility in Cardiac Resynchronisation Therapy. *Am J Cardiol.* 2004; 93:1500-1503.

[11] Nelson G S, Berger R D, Fetics B J, Talbot M, Spinelli J C, Hare J M, and Kass D A. Left Ventricular or Biventricular Pacing Improves Cardiac Function at Diminished Energy Cost in Patients With Dilated Cardiomyopathy and Left Bundle-Branch Block. *Circulation*. 2000; 102(25): 3053-3059.

[12] Blanc J J, Etienne Y, Gilard M, Mansourati J, Munier S, Boschat J, Benditt D G, Lurie K G. Evaluation of different ventricular pacing sites in patients with severe heart failure: results of an acute hemodynamic study. *Circulation.* 1997; 96:3273-3277.

[13] Ghali J K, Kadakia S, Bhatt A, et al. Survival of heart failure patients with preserved versus impaired systolic function: the prognostic implication of blood pressure. *Am Heart J.* 1992 April; 123(4 Pt 1):993-7.

[14] Cowie M R, Wood D A, Coats A J S, et al. Survival of patients with a new diagnosis of heart failure: a population based study. Heart. 2000; 83:505-510.

[15] Shamin W, Francis D P, Yousufuddin M, et al. Intraventricular conduction delay: a prognostic marker in chronic heart failure. *Int J Cardiol* 1999; 70:171-78.

[16] Davos C, Doehner W, Rauchhaus M, et al. Body Mass and Survival in Patients with Chronic Heart Failure without Cardiac Cachexia: The Importance of Obesity. *J Card Fail* 2003; 9:29-35.

[17] Bouvy M L, Heerdink E R, Leufkens H G M, Hoes A W. Predicting mortality in patients with heart failure: a pragmatic approach. *Heart* 2003; 89:605-609.

[18] Rouleau J L, Roecker E B, Tendera M, et al. Influence of Pretreatment Systolic Blood Pressure on the Effect of Carvedilol in Patients With Severe Chronic Heart Failure. The COPERNICUS study. *J Am Coll Cardiol* 2004; 43:1423-9.

[19] Ritter P, Dib J C, Lelievre T et al. Quick determination of the optimal AV delay at rest in patients paced in DDD mode for complete AV block. *EuroPACE* 1994; Vol 4, No 2:163.

[20] Ritter P, Padeletti L, Gillio-Mein L and Gaggini G. Determination of the optimal atrioventricular delay in DDD pacing. *EuroPACE* 1999; 1:126-130.

[21] Fischer W, Ritter P H. Cardiac pacing in clinical practice. *Berlin, Springer* 1998; 191.

[22] Jansen A H, Dantzig J, Bracke F A, et al. Determination of different echocardiographic methods for optimization of atrio-ventricular delay in cardiac resynchronization therapy. *Heart Rhythm.* 2004; Vol 1, No 1 (suppl):579.

[23] Leclerq C, Kass D A. Retiming the failing heart: principles and current clinical status of cardiac resynchronisation. *J Am Coll Cardiol*. 2002; 39:194-201.

[24] Cazeau S, Leclercq C, Layergne T, et al. The multisite stimulation in cardiomyopathies (MUSTIC) study investigators. Effects of multisite pacing in patients with heart failure and intraventricular conduction delay. *N Engl J Med* 2001; 344:873-880.

[25] Jais P, et al. Mid-term follow up of endocardial biventricular pacing. *PACE* 2000; 346:1845.

[26] Abraham W T, Fisher W G, Smith A L, et al. Cardiac resynchronization in chronic heart failure. *N Engl J Med* 2002; 246: 1845-53.

[27] Bristow M R, Saxon L A, Boehmer J, et al. Cardiac-resynchronization Therapy with or without an implantable Defibrillator in Advanced Chronic Heart Failure. *N Engl J Med.* 2004; 350:2140-50.

[28] Peňáz J Photoelectric measurement of blood pressure, volume and flow in the finger. Digest of the international Conference on Medicine and Biological Engineering, Dresden, 1973 p 104 (abstract).

[29] Wessling K H, De Wit B, Van der Hoeven G M, Van Goudover J and Settels J. Physiocal calibrating finger vascular physiology for Finapres. *Homeostasis* 1995; 36:67-82.

[30] Imholz B P M, Weiling W, Montfrans G A, Wesseling K H. Fifteen years experience with finger arterial pressure monitoring: assessment of the technology. *Cardiovasc. Res.* 1998; 38: 605-616.

[31] Davies L C, Francis D P, Jurak P, Kara T, Piepoli M, Coats A J S. Reproducibility of methods for assessing baroreflex sensitivity in normal controls and in patients with chronic heart failure. *Clin Sci (Lond)* 1999; 97:515-522.

[32] Jansen A H, Van Dantzig J, Bracke F A, et al. Determination of reliability of different echocardiographic methods for optimisation of atrio-ventricular delay in cardiac resynchronisation therapy. *Heart Rhythm* 2004; 1:579.

[33] Romano S A, Pistolasi M. Assessment of Cardiac Output from systolic arterial pressure in humans. *Crit Care Med* 2002; 30:1834-1841.

The invention claimed is:

1. A pacemaker programming apparatus for use with a pacemaker, the pacemaker programming apparatus comprising:

a monitoring device capable of determining a haemodynamic measure of an individual at each heart beat of the individual and generating a haemodynamic measure indication signal related to the haemodynamic measure; and a processor that is configured for:
adjusting the pacemaker to alternate a setting of a first attribute of the pacemaker between a reference setting and a test setting, and
receiving the haemodynamic measure indication signal, and
generating a pacemaker programming signal, for transmitting to the pacemaker, in response to the haemodynamic measure indication signal determined in the individual at the reference setting and at the test setting;
wherein the processor is also configured for instructing the pacemaker to raise the heart rate of the individual when the first attribute is at the reference setting, and when the first attribute is at the test setting.

2. The pacemaker programming apparatus according to claim 1 wherein the monitoring device is configured for:
determining the haemodynamic measure of an individual at each heart beat of the individual, and
generating the haemodynamic measure indication signal related to the haemodynamic measure.

3. The pacemaker programming apparatus according to claim 1 wherein the monitoring device comprises one of (i) a pulse oximeter and (ii) a bio-impedance monitor.

4. The pacemaker programming apparatus according to claim 1, wherein the processor is configured to generate the pacemaker programming signal by determining a change in the haemodynamic measure, due to an adjustment of the setting of the first attribute of the pacemaker.

5. The pacemaker programming apparatus according to claim 1, further comprising:
   a communication device for transmitting the pacemaker programming signal to the pacemaker.

6. The pacemaker programming apparatus according to claim 1, wherein the monitoring device is a non-invasive monitoring device.

7. The pacemaker programming apparatus according to claim 6 wherein the monitoring device comprises:
   a contractible cuff for receiving a body extremity of an individual;
   a light source directable upon a body extremity received in the contractible cuff; and
   a light sensor for detecting light from the light source, the light sensor being located such that a body extremity received in the contractible cuff interposes between the light source and the light sensor, the light sensor being capable of generating the haemodynamic measure indication signal in response to the intensity of light detected from the light source.

8. The pacemaker programming apparatus according to claim 1, further comprising an artefact sensor for detecting at least one of (a) the phase of respiration and (b) a body movement of the individual, the artefact sensor being in communication with the processor.

9. The pacemaker programming apparatus according to claim 8, wherein the artefact sensor comprises a strain gauge.

* * * * *